(12) United States Patent
Kokish

(10) Patent No.: US 9,668,814 B2
(45) Date of Patent: Jun. 6, 2017

(54) INFINITELY ROTATABLE TOOL WITH FINITE ROTATING DRIVE SHAFTS

(71) Applicant: Hansen Medical, Inc., Mountain View, CA (US)

(72) Inventor: Arkady Kokish, Los Gatos, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1079 days.

(21) Appl. No.: 13/788,440

(22) Filed: Mar. 7, 2013

(65) Prior Publication Data

US 2014/0257326 A1  Sep. 11, 2014

(51) Int. Cl.
| A61B 17/00 | (2006.01) |
| A61B 19/00 | (2006.01) |
| A61B 34/30 | (2016.01) |

(52) U.S. Cl.
CPC .......... *A61B 19/2203* (2013.01); *A61B 34/30* (2016.02); *A61B 2017/00477* (2013.01); *A61B 2034/301* (2016.02); *Y10T 29/49002* (2015.01); *Y10T 74/18096* (2015.01)

(58) Field of Classification Search
CPC ............. A61B 34/30; A61B 2034/301; A61B 2034/302; A61B 2034/303; A61B 2034/304; A61B 2034/71; A61B 2034/715

See application file for complete search history.

(56) References Cited

U.S. PATENT DOCUMENTS

| 5,398,691 A | 3/1995 | Martin et al. |
| 5,408,409 A | 4/1995 | Glassman et al. |
| 5,524,180 A | 6/1996 | Wang et al. |
| 5,631,973 A | 5/1997 | Green |
| 5,713,946 A | 2/1998 | Ben-Haim |
| 5,749,362 A | 5/1998 | Funda et al. |
| 5,859,934 A | 1/1999 | Green |
| 5,876,325 A | 3/1999 | Mizuno et al. |
| 5,951,475 A | 9/1999 | Gueziec et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,726,675 B1 * | 4/2004 | Beyar ............... A61M 25/0105 600/106 |
| 7,155,315 B2 | 12/2006 | Niemeyer et al. |
| 2006/0025676 A1 | 2/2006 | Viswanathan et al. |
| 2008/0039255 A1 * | 2/2008 | Jinno .................. A61B 17/062 474/148 |
| 2011/0288573 A1 * | 11/2011 | Yates ............... A61B 17/07207 606/170 |

FOREIGN PATENT DOCUMENTS

WO   03086190 A1   10/2003

* cited by examiner

*Primary Examiner* — Anh Dang

(74) *Attorney, Agent, or Firm* — Knobbe, Martens, Olson and Bear, LLP

(57) ABSTRACT

A catheter rotation drive apparatus includes first and second drives that are engageable to an output shaft. When the first drive is engaged to the output shaft and rotated, the output shaft rotates in an output rotation direction, and when the second drive is engaged to the output shaft and rotated, the output shaft rotates in the output rotation direction.

9 Claims, 8 Drawing Sheets

INFINITELY ROTATABLE TOOL WITH FINITE ROTATING DRIVE SHAFTS

BACKGROUND

Robotic interventional systems and devices are well suited for performing minimally invasive medical procedures as opposed to conventional techniques wherein the patient's body cavity is open to permit the surgeon's hands access to internal organs. Advances in technology have led to significant changes in the field of medical surgery such that less invasive surgical procedures, in particular, minimally invasive surgery (MIS), are increasingly popular.

A MIS is generally defined as a procedure that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

MIS apparatus and techniques have advanced to the point where an elongated catheter instrument is controllable by selectively operating tensioning control elements within the catheter instrument. In one example, four opposing directional control elements wind their way to the distal end of the catheter which, when selectively placed in and out of tension, cause the distal end to steerably maneuver within the patient. Control motors are coupled to each of the directional control elements so that they may be individually controlled and the steering effectuated via the operation of the motors in unison.

However, in some clinical situations, it is not possible to use an elongate instrument with multi directional control elements. For instance, in some MIS procedures a micro-catheter is used that does not have any steering element. Elongate instruments having multiple driving elements are typically larger in diameter and sometimes cannot pass through the naturally occurring lumens within the body (e.g., veins or arteries). In these MIS procedures, navigation can be performed with a much simpler non-steerable pre-curved catheter. These catheters can be navigated by simply rotating the pre-curved tip, while feeding the catheter into the lumen.

Robotic systems that are designed with directional control often have limited capability to rotate the entire elongate instrument. It is not necessary to rotate the entire instrument because there is complete direction control at the tip by selectively placing the directional control elements in and out of tension. However, if non deflectable instruments are attached to these robotic systems, greater rotational capability of the entire device is needed. If multiple control motors are present in a robot system that is typically used for steering a steerable catheter, it can be inconvenient or not possible to switch out the multiple motor control system, and enable it to use the simpler non-steerable device to provide catheter rotation capability.

As such, there is a need for a robotic system that can activate the directional control elements when steerable devices are attached to it and can also be used to rotate the entire device when non steerable devices are attached to it.

SUMMARY

A catheter rotation drive apparatus includes first and second drives that are engageable to an output shaft. When the first drive is engaged to the output shaft and rotated, the output shaft rotates in an output rotation direction, and when the second drive is engaged to the output shaft and rotated, the output shaft rotates in the output rotation direction.

A method of fabricating a rotatable catheter includes providing first and second drive shafts that are engageable to an output shaft, wherein when the first drive shaft is engaged to the output shaft and rotated, the output shaft rotates in an output rotation direction, and when the second drive shaft is engaged to the output shaft and rotated, the output shaft rotates in the output rotation direction.

A robotically controlled surgical system includes a robotic instrument driver, wherein the robotic instrument driver is controllable by an operator workstation. The robotic instrument driver includes a rotatable output shaft extending from a housing, and a plurality of input drives within the housing that are each rotatable about respective drive axes and coupled to rotatable shafts of the robotic instrument driver. When a first of the input drives is coupled with the output shaft, and when the first input drive is rotated, the output shaft is caused to rotate in an output rotational direction, and when a second of the input drives is coupled with the output shaft, and when the second input drive is rotated, the output shaft is caused to rotate in an output rotational direction.

BRIEF DESCRIPTION

DETAILED DESCRIPTION

Figure 1:
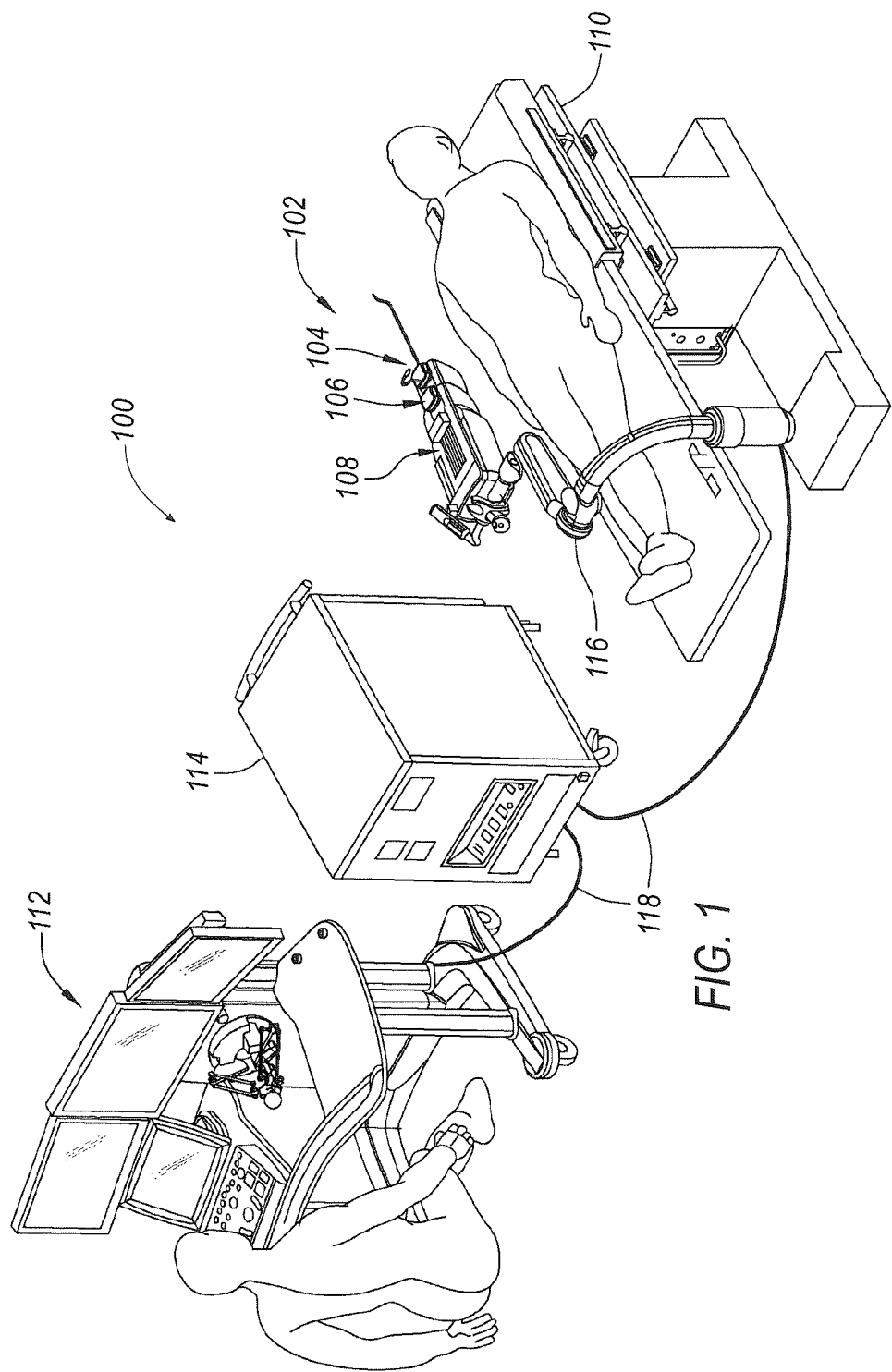
FIG. 1 is an illustration of a robotically controlled surgical system, according to one exemplary illustration.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver"). During use, a patient is positioned on an operating table or surgical bed 110 (generally referred to as "operating table") to which robotic instrument driver 108 is coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
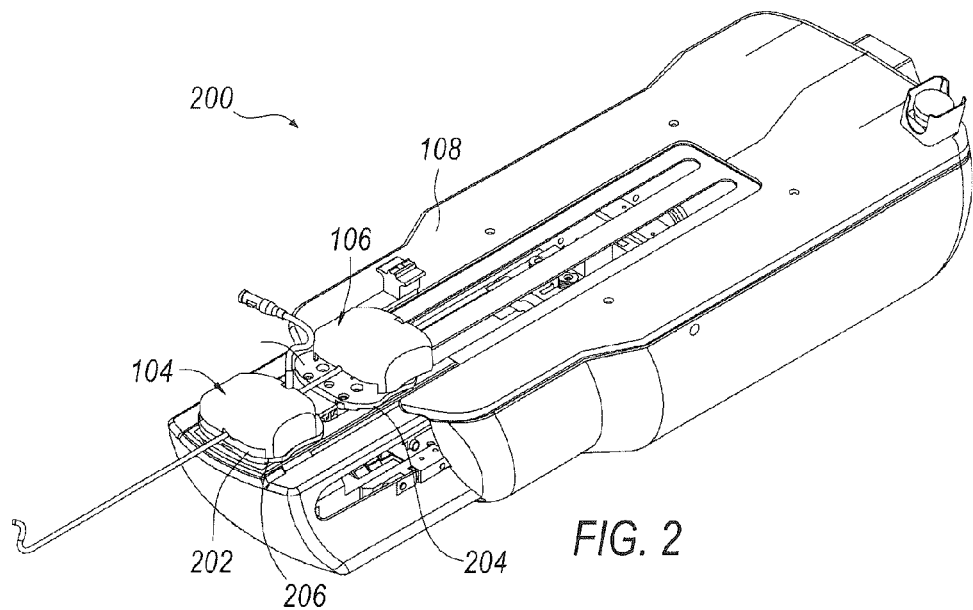
FIG. 2 is an illustration of an exemplary catheter assembly of the surgical system of FIG. 1.

Referring now to FIG. 2, an instrument assembly 200 includes sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to mounting plates 204, 206 are driven forwards and backwards on bearings. As a result, a catheter coupled to guide catheter instrument 106 and sheath instrument 104 can be controllably manipulated while inserted into the patient, as will be further illustrated. Additional instrument driver 108 motors may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively.

Figure 3:
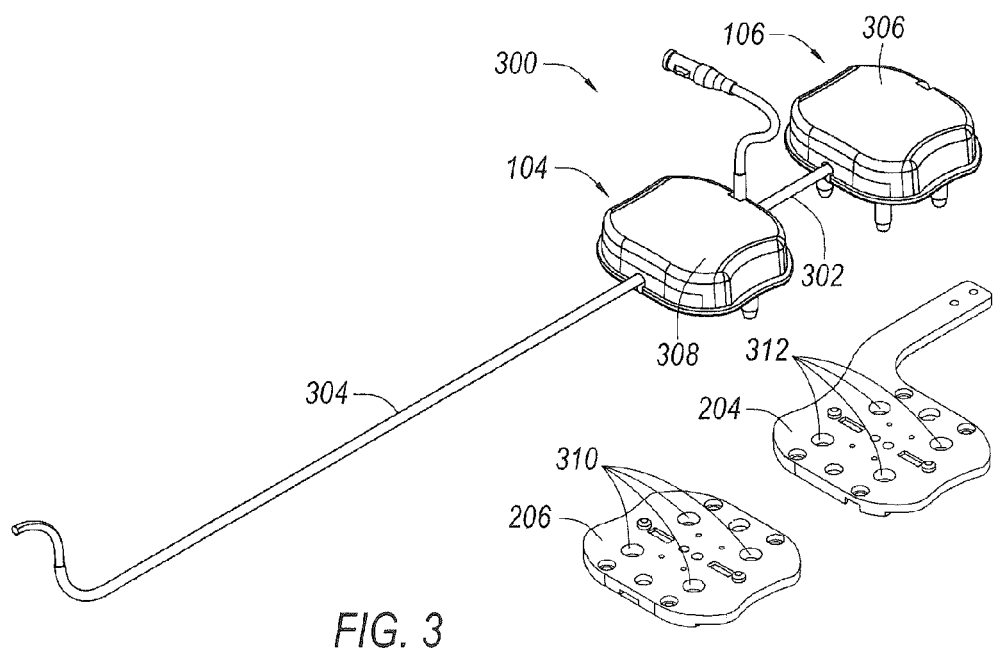
FIGS. 3 and 4 are illustrations of components of the catheter assembly of FIG. 2.

Referring to FIG. 3, an assembly 300 includes sheath instrument 104 and guide or catheter instrument 106 positioned over their respective mounting plates 206, 204. In the illustrated example, a guide catheter instrument member 302 is coaxially interfaced with a sheath catheter member 304 by inserting the guide catheter instrument member 302 into a working lumen of sheath catheter member 304. Sheath catheter member 304 includes a distal end that is manipulable via assembly 300, as will be further discussed in FIG. 5. Sheath instrument 104 and guide or catheter instrument 106 are coaxially disposed for mounting onto instrument driver 108. However, it is contemplated that a sheath instrument 108 is used without guide or catheter instrument 106, or guide or catheter instrument 106 is used without sheath instrument 104 and may be mounted onto instrument driver 108 individually.

When a catheter is prepared for use with an instrument, its splayer is mounted onto its appropriate interface plate. In this case, sheath splayer 308 is placed onto sheath interface plate 206 and a guide splayer 306 is placed onto guide interface plate 204. In the illustrated example, each interface plate 204, 206 has respectively four openings 310, 312 that are designed to receive corresponding drive shafts 314, 316 (FIG. 4 illustrates an underside perspective view of shafts 314, 316) attached to and extending from the pulley assemblies of the splayers 308, 306).

Figure 5:
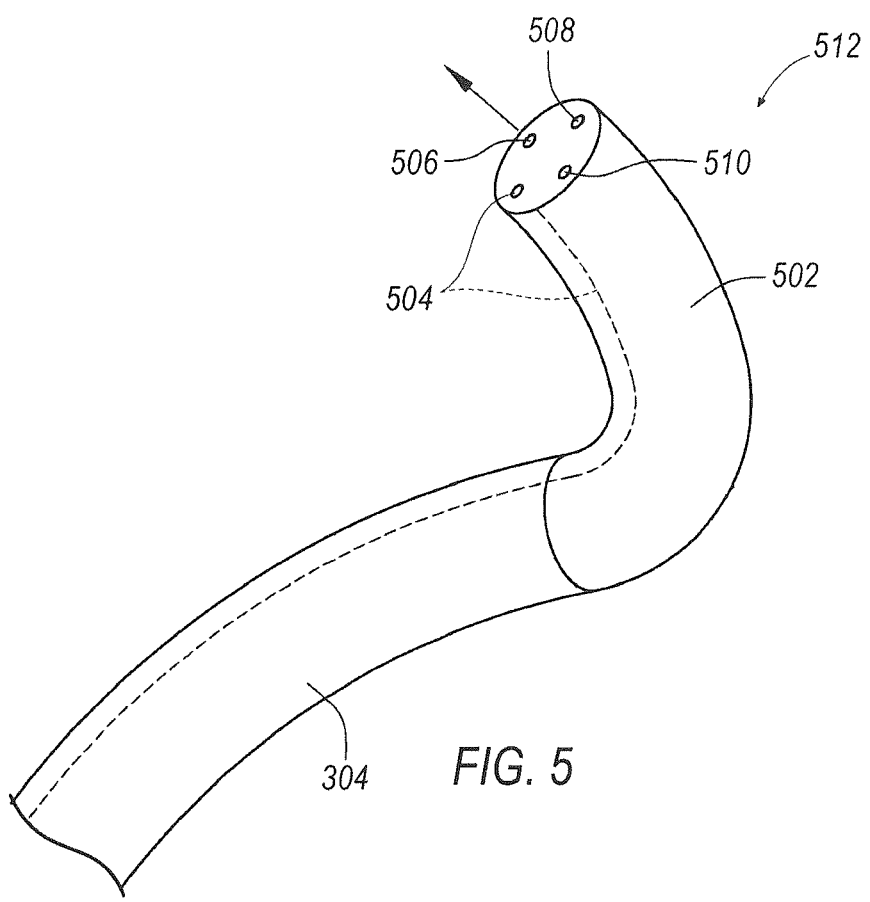
FIG. 5 illustrates a distal end of an exemplary catheter that is controllable by internal control elements.

Operator workstation 112 may include a computer monitor to display a three dimensional object, such as a catheter instrument 502 as illustrated in FIG. 5. Catheter instrument 502 may be displayed within or relative to a three dimensional space, such as a body cavity or organ, e.g., a chamber of a patient's heart. In one example, an operator uses a computer mouse to move a control point around the display to control the position of catheter instrument 502.

Figure 4:
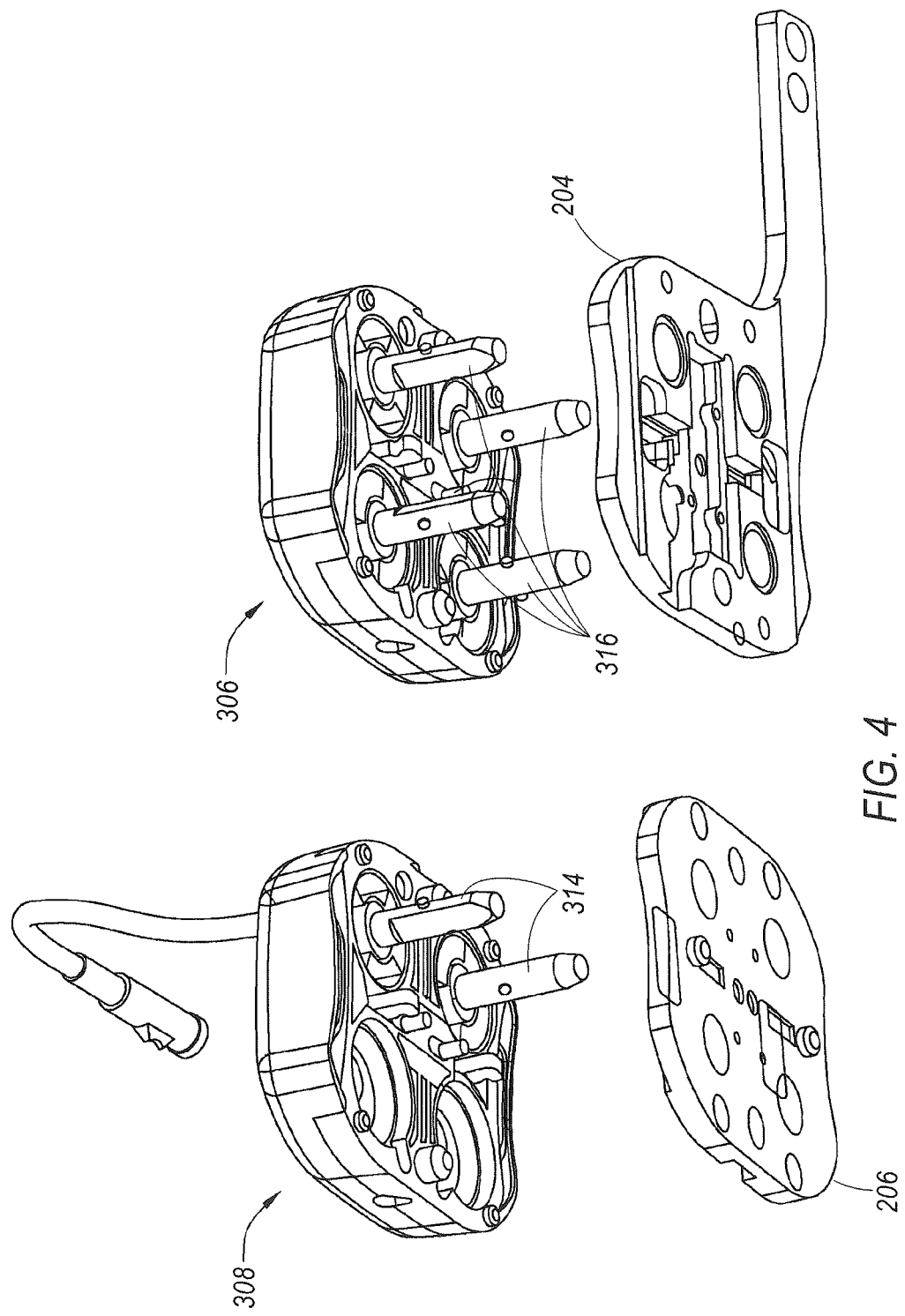

Turning now to FIGS. 3 and 4, an exemplary sheath instrument 104 and catheter instrument 106 are described in further detail. According to one exemplary illustration, sheath instrument 104 may include a sheath splayer 308 having drive shafts 314. Catheter instrument 106 may include a guide splayer 306 having drive shafts 316. Drive shafts 316 are each coupled to a respective motor within instrument driver 108 (motors not shown). When 4-wire catheter 304 is coupled to instrument driver 108, each drive shaft 316 thereof is thereby coupled to a respective wire 504-510 (see FIG. 5). As such, a distal end 512 of catheter 304 can be articulated and steered by selectively tightening and loosening wires 504-510. Typically, the amount of loosening and tightening is slight, relative to the overall length of catheter 304. That is, each wire 504-510 typically need not be tightened or loosened more than perhaps a few centimeters. As such, the motors that tighten/loosen each wire typically do not rotate more than, for example, ¾ of a rotation.

Splayer 314 and drive shaft 316 have pin/screw combinations and flats and. These features act as a key and match with corresponding features in the output shafts of the robotic system. The robotic system presents its output shaft in a fixed orientation upon boot up to receive the keyed pins of the splayer. A typical motor and gear box in a robotic system includes a hard stop in a gear box that allows the motor to find a home point every time the system is booted up. The encoder can then index from this point and position the keyed output shafts at any desired location. It is beneficial for the output shafts of the robotic system to rotate less than one full revolution, which enables a hard stop to be designed into the rotation mechanism.

Returning now to the challenge of using this robotic system to rotate a non steerable catheter. Because microcatheters are generally not torsionally stiff, and because of their relatively long length, the minimal rotations on the output shafts is generally not adequate to provide the rotational motion needed at a distal end thereof.

Figure 6A:
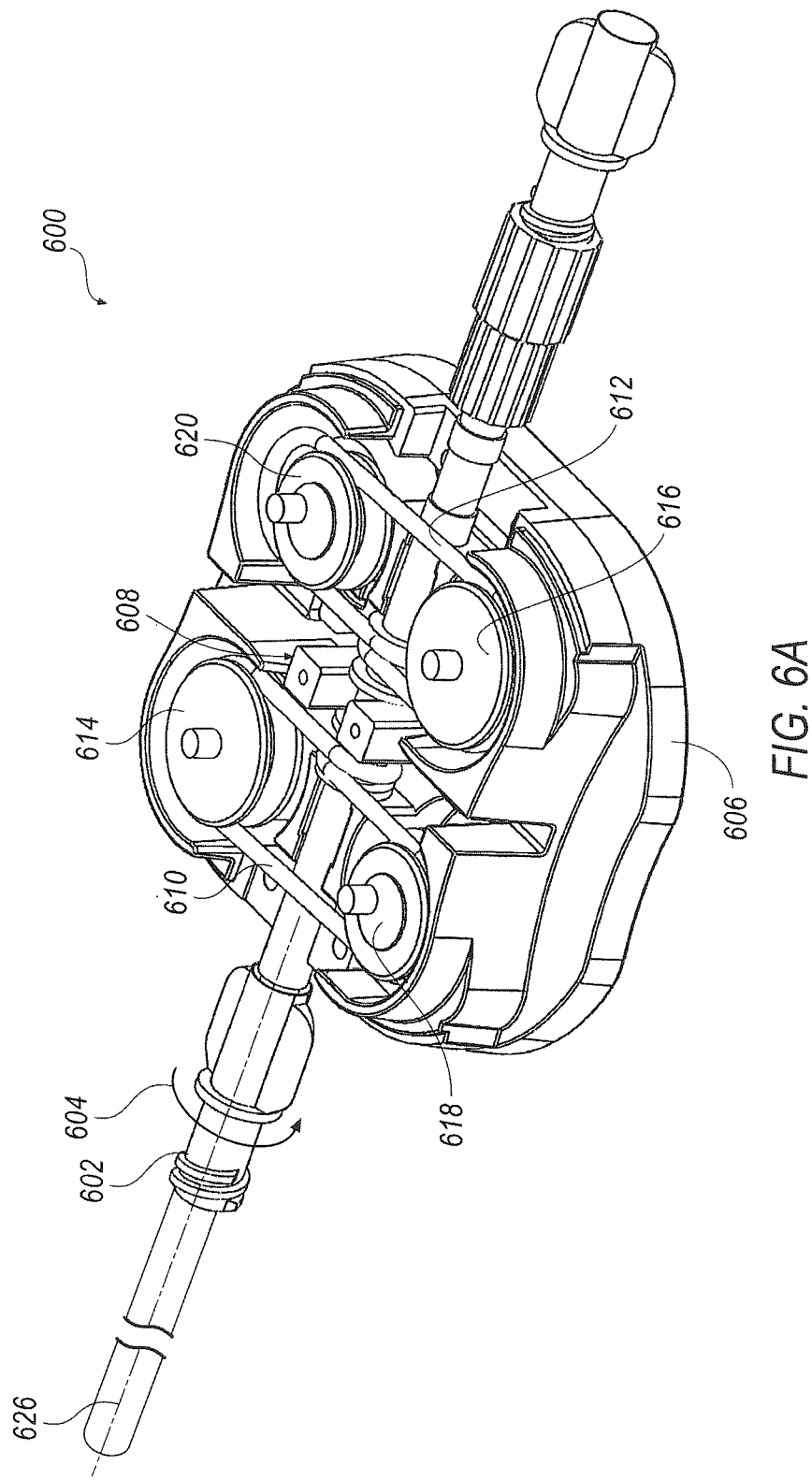
FIGS. 6A and 6B illustrate an exemplary catheter rotation device or drive apparatus.
Figure 6B:
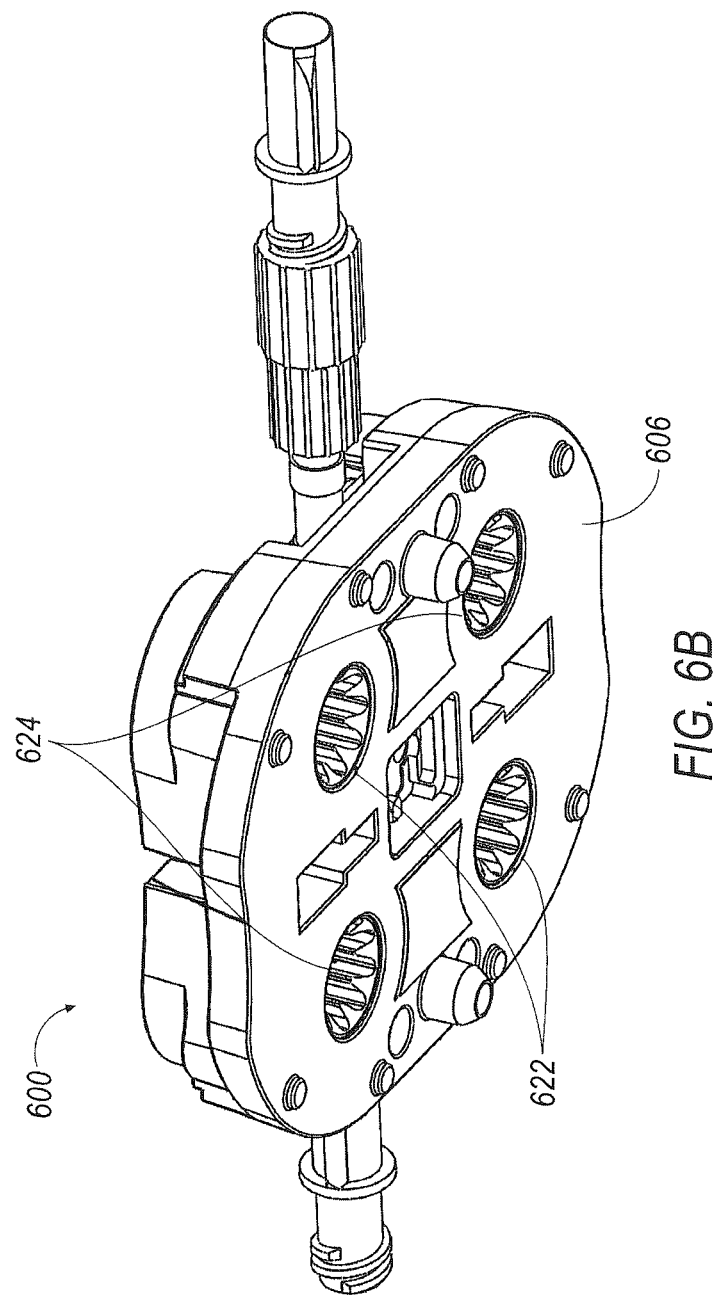

Referring to FIGS. 6A and 6B, an exemplary catheter rotation device or drive apparatus 600 is illustrated. Device 600 is an exemplary catheter instrument 106 that is positionable on instrument driver 108. Device 600 includes an output shaft 602 that is infinitely rotational in an output rotational circumferential direction 604, using the motors that tighten/loosen each wire. In one exemplary illustration, infinite rotational motion can be imparted even though the motors rotate through approximately ¾ of a rotation each. Output shaft 602 extends through a body or support structure 606, and output shaft 602 is supported via, in the example illustrated, at least one bearing 608. Bearing 608 allows free rotation of output shaft 602 relative to support structure 606. Output shaft 602 is rotationally driven in output direction 604 through a first belt or O-ring 610 and a second belt or O-ring 612. Device 600 includes a first drive pulley 614 about which first O-ring 610 is wrapped, and a second drive pulley 616 about which second O-ring 612 is wrapped. Device 600 also includes a first engagement or eccentric shaft or shaft with a cam surface 618 about which first O-ring 610 is wrapped, and a second engagement or eccentric shaft or shaft with a cam surface 620 about which second O-ring 616 is wrapped. The first and second engagement or eccentric shafts 618, 620 enable engagement of drive pulleys to drive output shaft 602, as will be further described.

As stated, drive pulleys 614, 616 and eccentric shafts 618, 620 are mechanically coupled to drive shafts, such as drive shafts 316 as shown in guide splayer 306. Incidentally, although drive shafts 316 are shown extending into guide splayer 306 in FIGS. 3 and 4, it is contemplated and understood that drive shafts 316 may instead be inserted into and remain in sheath instrument 108. As such, referring to FIG. 6B, drive shafts 316 are insertable into input shaft drives 622 and into input eccentric drives 624. Input shaft drives 622 are rotatable about respective drive axes that are approximately parallel to one another, and input drive shafts 622, as illustrated, are approximately orthogonal to a rotational axis 626 about which output rotational circumferential direction 604 rotates. Eccentric shafts 618, 620 are selectively engaged and disengaged (or unengaged) such that when one is engaged and tightens its O-ring, at the same time the other eccentric shaft is disengaged (or unengaged) and its O-ring is loose. That is, a drive pulley may be coupled to shaft 602 with its eccentric shaft engaged, while the other drive pulley may be decoupled from shaft 602 with its eccentric shaft disengaged.

Figure 7:
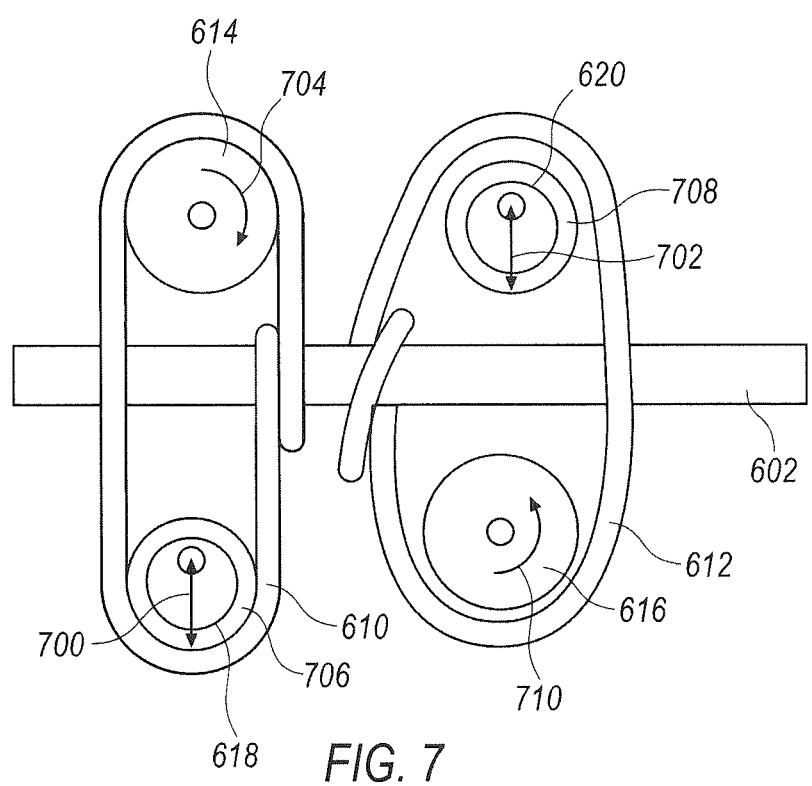
FIG. 7 illustrates a plan view showing the engagement and disengagement of drive shafts via eccentric shaft operation, according to one exemplary approach.

FIG. 7 illustrates a plan view showing the engagement and disengagement of drive shafts via eccentric shaft operation, according to an exemplary illustration. In FIG. 7, eccentric shaft 618 is shown in its rotated/engaged position such that its major eccentric dimension 700 is located away from shaft 602. With eccentric shaft 618 located accordingly, first O-ring 610 is thereby tightened about shaft 602 and also about drive pulley 614. The length of O-ring 610 is designed such that when the eccentric shaft creates the longest path for the O-ring, the O-ring is tight. At the same time, eccentric shaft 620 is in its rotated/dis-engaged position such that its major eccentric dimension 702 is located toward shaft 602. With eccentric shaft 620 located accordingly, second O-ring 612 is thereby loosened about shaft 602 and also about drive pulley 616. Under this arrangement, drive pulley 614 is caused to rotate, in this embodiment, ¾ of a turn in one direction 704 (which in one example is the rotational angular capability of drive pulley 614 and also of other rotational elements 616, 618, 620 driven by drive shafts 316). This causes shaft 602 to rotate via first O-ring 610 and about a rotational axis that is approximately orthogonal to a rotation axis of drive pulley 614. O-ring 610 also is driven relative to eccentric shaft 618 via a first wheel 706 (that is, first wheel 706 rotates relative to eccentric shaft 618).

Because eccentric shaft 620 is disengaged, rotation of output shaft 602 will not frictionally affect second O-ring 612. Further, because each drive pulley 614, 616 is rotatable about a limited rotational angle (¾ of a rotation in this example), while drive pulley 614 is causing O-ring 610 to engage and rotate output shaft 602, the other drive pulley 616 is retracting back through its retraction rotation angle 710.

After completion of the illustrated arrangement of FIG. 7, the process is reversed. That is, after drive pulley 614 reaches the end of its angular travel 704, and after drive pulley 616 has retracted back through its angular travel 710, then both eccentric shafts 618, 620 are reversed from the arrangement shown in FIG. 7 such that O-ring 610 is loose and O-ring 612 is tight. As such, drive pulley 616 is then caused to rotate in a drive angular direction that is opposite that of retraction direction 710, causing output shaft 602 to rotate in the same angular direction as that in the previous steps, and while wheel 708 is driven relative to eccentric shaft 620. Likewise, while drive shaft 616 is rotating (and causing output shaft 602 to rotate), the other drive pulley 614 is caused to retract in its direction opposite that shown as 704. In such fashion, the rotation sequence is repeated back and forth between drive pulleys and eccentric shafts such that output shaft 602 is rotated in the same angular direction for each step in the process. Likewise, it is contemplated that the entire operation can be reversed if rotation in the opposite direction is commanded by the user. The output shaft may also be caused to rotate in the other angular direction than that shown as angular direction 604 in FIG. 6A, depending on when the eccentric shafts are engaged and the angle of rotation of their respective drive pulleys. Thus, drive shaft 602 may be rotated in one angular direction during one set of conditions (i.e., engagement of each eccentric shaft and each drive pulley) or drive shaft 602 may be rotated in the opposite angular direction during an opposite set of conditions. Accordingly, infinite rotational motion (that is, repeated output rotation in one desired rotational direction) may be imparted by the drive pulleys 614, 616 in both directions even though neither pulley 614, 616 rotates even one full 360 rotation about its associated drive shaft.

Output shaft 602 may be coupled to a catheter. As stated, in a catheter that does not have steering wires such as in catheter 304 described earlier, a catheter without steering wires such as catheter 622 illustrated in FIG. 6A may be rotated infinitely in output direction 604 or in a direction opposite to output direction 604. Further, although the operation of driving one drive shaft and retracting the other drive shaft is described as occurring at essentially the same time, it is contemplated that the operation may be sequential instead. That is, the steps may be sequentially performed such that the drive shaft is driven during a first time period, and the other drive shaft is retracted during a second and subsequent time period. In other words, the two operations of driving one shaft and retracting the other need not be simultaneous.

In addition, it is contemplated that the operation of driving and retracting each drive shaft may be controlled such that the rotation of output shaft is not only infinite, but continuous as well. That is, a controller may be configured to operate one of the drive shafts at a first speed, and retraction of the other may be at a second and faster speed. In such fashion the retraction of the drive shaft may be timed so that it is next ready to drive the drive shaft when the other drive shaft reaches its limit of rotational travel.

Figure 8:
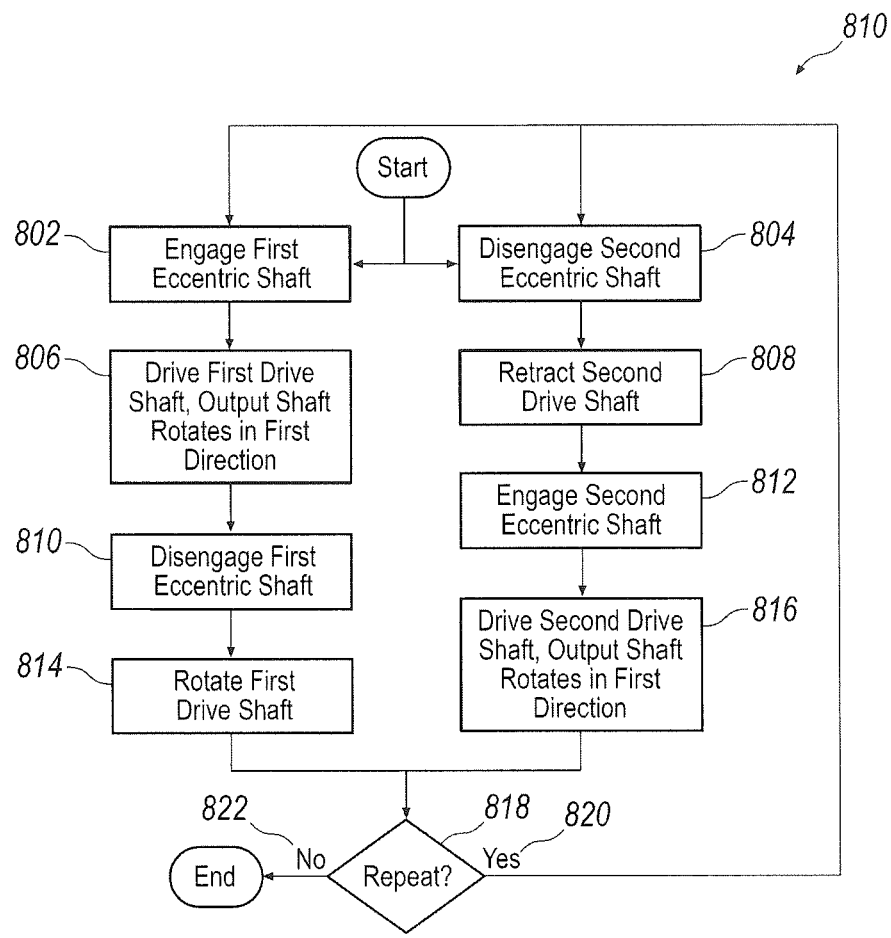
FIG. 8 illustrates a process flow diagram for an exemplary method for operating drive shafts and eccentric shafts.

Turning now to FIG. 8, a process flow diagram of an exemplary method of using a catheter is illustrated. After starting, first eccentric shaft 618 is engaged at block 802 and second eccentric shaft 620 is disengaged at block 804. While first eccentric shaft 618 is engaged, first drive shaft 614 is driven, causing output shaft 602 to rotate in a first direction, such as direction 604, at block 806. While second eccentric shaft 620 is disengaged, second drive shaft 616 is retracted at block 808. First eccentric shaft 618 is disengaged at block 810 and second eccentric shaft 620 is engaged at block 812. While second eccentric shaft 620 is engaged, second drive shaft 616 is driven, causing output shaft 602 to rotate in the first direction, such as direction 604, at block 816. While first eccentric shaft 618 is disengaged, first drive shaft 614 is retracted at block 814. At block 818, if it is desired to repeat the process 820, then process control returns to blocks 802, 804 to continue through another cycle. If not 822, the process ends.

Operator workstation 112 may include a computer or a computer readable storage medium implementing the operation of drive and implementing process 800. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A robotically controlled surgical system, comprising:
   a robotic instrument driver configured to articulate a steerable catheter, the robotic instrument driver comprising rotatable shafts operatively coupleable to respective drive shafts of a splayer of the steerable catheter and configured to rotate the respective drive shafts of the splayer to tension respective directional control elements coupled thereto; and
   a non-steerable catheter rotation device positioned on the robotic instrument driver, wherein the non-steerable catheter rotation device comprises:
      an output shaft extending from a housing;
      a first input drive pair within the housing and comprising a first eccentric shaft; and
      a second input drive pair within the housing and comprising a second eccentric shaft,
      wherein each of the first input drive pair and the second input drive pair is rotatable about respective drive axes and is coupled to a respective one of the rotatable shafts of the robotic instrument driver,
      wherein a first rotation of the first and second eccentric shafts results in engagement of the first input drive pair with the output shaft and disengagement of the second input drive pair with the output shaft, and a second rotation of the first and second eccentric shafts results in engagement of the second input drive pair with the output shaft and disengagement of the first input drive pair with the output shaft, and
      wherein:

when the first input drive pair is engaged with the output shaft and rotated, the output shaft is caused to rotate in an output rotational direction, and when the second input drive pair is engaged with the output shaft and rotated, the output shaft is caused to rotate in the output rotational direction.

2. The surgical system of claim 1, wherein:

the first input drive pair further comprises a first drive pulley coupled to the first eccentric shaft via a first belt;

the second input drive pair further comprises a second drive pulley coupled to the second eccentric shaft via a second belt, and when the first input drive pair is engaged and the first drive pulley is rotated in its drive direction, the output shaft is caused to rotate via the first belt in a first rotational direction.

3. The surgical system of claim 2, wherein when the second input drive pair is unengaged, the second drive pulley is rotatable in its retraction direction without causing rotation of the output shaft.

4. The surgical system of claim 2, wherein when the second input drive pair is engaged and the second drive pulley is rotated in its drive direction, the output shaft is caused to rotate in the first rotational direction via the second belt.

5. The surgical system of claim 2, wherein the first belt is a first O-ring, and the second belt is a second O-ring.

6. The surgical system of claim 5, wherein:

the first O-ring is wrapped about:
the first eccentric shaft;
the first drive pulley; and
the output shaft; and the second O-ring is wrapped about:
the second eccentric shaft;
the second drive pulley; and
the output shaft.

7. The surgical system of claim 2, wherein an overall output shaft rotation is greater than an input rotation of either of the first and second drive pulleys.

8. The surgical system of claim 2, wherein the first and second drive pulleys are each rotatable no more than one full revolution.

9. The surgical system of claim 1, wherein the output shaft is rotated continuously through engagement of the first input drive pair and engagement of the second input drive pair.

* * * * *